United States Patent [19]

Makhoul et al.

[11] Patent Number: 5,291,882

[45] Date of Patent: Mar. 8, 1994

[54] MULTI-LUMEN ITPV ENDOTRACHEAL TUBE

[76] Inventors: Imad R. Makhoul, 240 S. Doheny Dr., 190 306, Beverly Hills, Calif. 90211; Joel E. Berkeland, 27846 Audrey Ct., Canyon Country, Calif. 91351

[21] Appl. No.: 881,221

[22] Filed: May 11, 1992

[51] Int. Cl.$^5$ ............................................. A61M 16/00
[52] U.S. Cl. ........................... 128/207.14; 128/200.26; 128/207.15
[58] Field of Search ........ 128/200.26, 204.24, 204.25, 128/207.14, 207.15

[56] References Cited

U.S. PATENT DOCUMENTS

| | | | |
|---|---|---|---|
| 2,862,498 | 12/1958 | Weekes | 128/207.14 |
| 3,734,094 | 5/1973 | Calinog | 128/207.15 |
| 4,291,691 | 9/1981 | Cabal et al. | 128/207.14 |
| 4,334,534 | 6/1982 | Ozaki | 128/207.15 |
| 4,383,534 | 5/1983 | Peters | 128/207.15 |
| 4,519,388 | 5/1985 | Schwanbom et al. | 128/207.15 |
| 4,573,462 | 3/1986 | Baum | 128/204.25 |
| 4,596,247 | 6/1986 | Whitwan et al. | 128/204.25 |
| 4,646,733 | 3/1987 | Stroh et al. | 128/207.15 |
| 4,681,100 | 7/1987 | Brychta et al. | 128/204.25 |
| 4,850,371 | 7/1989 | Broadhurst et al. | 128/207.15 |
| 4,976,261 | 12/1990 | Gluck et al. | 128/207.15 |
| 5,186,167 | 2/1992 | Kolobow | 128/207.14 |

Primary Examiner—Edgar S. Burr
Assistant Examiner—Aaron J. Lewis
Attorney, Agent, or Firm—Merchant, Gould, Smith, Edell, Welter & Schmidt

[57] ABSTRACT

Intratracheal pulmonary ventilation is introduced to the distal end of an endotracheal tube by one or more intratracheal pulmonary ventilation tubes located in the wall of an endotracheal tube. The direction of flow of the intratracheal pulmonary ventilation is directed away from the distal end of said endotracheal tube, towards the proximal end of said endotracheal tube. The flow through the intratracheal pulmonary ventilation tube reduces the amount of carbon dioxide by replacing the gas located between the distal end of the endotracheal tube and the proximal end of the endotracheal tube where the endotracheal tube is connected to an artificial ventilation system.

14 Claims, 5 Drawing Sheets

MULTI-LUMEN ITPV ENDOTRACHEAL TUBE

FIELD OF THE INVENTION

The present invention relates generally to Endotracheal Tubes, and has particular application to Endotracheal Tubes provided with augmented air flow.

BACKGROUND OF THE INVENTION

As the result of trauma or lung disease, it occasionally becomes difficult for particular individuals to breathe without the assistance of a respirator or other mechanical apparatus which tends to force air into the lungs of an individual to assist or substitute for the normal inspiration (or inhalation). A respirator or other mechanical means is also generally used to extract air from the lungs of the individual, substituting for the normal expiration (or exhalation) portion of the respiration (or breathing) cycle.

A variety of devices are used to interconnect a respirator, or mechanical breathing means to the air passage of a patient. These devices typically include tubes which are positioned along the laryngotracheal airway between the mouth or nose and the lungs of the patient. A particular class of this type of tube is referred to as an endotracheal tube which is preferably routed through the mouth of a patient and oriented such that the opening of the tube within the body cavity is located immediately above the lungs of the patient.

Examples of this type of endotracheal tube include U.S. Pat. No. 4,334,534 issued to Ozaki in which an endotracheal tube having three internal tubes is inserted through the mouth of the patient and manipulated into the esophageal airway to allow it to be positioned and used for ventilation. The Ozaki device is intended for use as an emergency medical apparatus to be applied by a paramedic, emergency medical technician, or other emergency response personnel in emergency field applications. The Ozaki invention has an inflatable cuff which can be used to form a seal between the walls of the endotracheal tube and the trachea or esophagus depending on where the device is located when it is inserted into the patient. The Ozaki device can also be adapted for use in conjunction with a stomach drain tube to evacuate the contents of the stomach when the Ozaki device is appropriately positioned.

U.S. Pat. No. 4,519,388 issued to Schwanbom, et al. describes a respirator device which has one end located in the trachea of a patient, and is combined with the use of a venturi tube to alleviate problems caused by coughing spells and reduced barotraumas. Schwanbom maintains a continuous vacuum in order to accomplish these goals.

U.S. Pat. No. 4,646,733 issued to Stroh, et al. describes a flexible endotracheal tube through which a second tube can be inserted for directing respiratory air pulses into the trachea of the patient. Stroh employs either mechanical rotary slide valves or electrically operated valves in order to activate the device.

U.S. Pat. No. 4,850,371 issued to Broadhurst, et al. describes a device used to monitor the quantity and composition of inhaled and expired gases, and to calculate the pulmonary function and cardiac output based on the inhaled and expired gas composition. Broadhurst employs an endotracheal tube which incorporates a miniature mass spectrometer to continuously and rapidly measure the gas content. Broadhurst employs an endotracheal tube with several internal passage ways through which gas is sampled.

U.S. Pat. No. 4,573,462, issued to Baum, describes a respiratory system which incorporates a pressure relief valve. An endotracheal tube having a single tube is employed in Baum. The gas cycle to the patient is passed through a carbon dioxide absorber in order to purify the content of the air supplied to a patient.

U.S. Pat. No. 4,681,100, issued to Brychta, et al., employs an endotracheal tube having several different tubes contained within it in order to allow cleaning the air passages of a patient without interrupting ventilation. The Brychta invention can be used in conjunction with two ventilation generators to provide gas supplying having different over pressures.

U.S. Pat. No. 4,596,247, issued to Whitwam, et al., describes a respirator in which the gas inlet and gas outlet sections are spaced apart in the respirator. The respirator is then connected to a standard endotracheal tube which is inserted into a patient.

U.S. Pat. No. 4,291,691, issued to Cabal, et al., describes an adaptor which is inserted between a respirator and the artificial airway of a patient. The adaptor allows one or more additional tubes to be inserted through the main cavity of a single endotracheal tube without disturbing the seal of the main endotracheal tube.

U.S. Pat. No. 3,734,094, issued to Kolobow, describes a multipurpose esophageal instrument which can be used for suctioning out secretions from the stomach. The Kolobow device also includes a variety of electrodes located on the esophageal tube in order to sense the heart rate and provide an electrocardiogram (EKG) which is sensed from within the body cavity of the patient.

U.S. Pat. No. 4,383,534, issued to Peters, describes an endotracheal tube which is augmented with a temperature detector, electrocardiogram detector, and audio sensing means to monitor the sound of the heart and respiration. Blood pressure sensing means is also connected to the device.

There is typically a trade off between the diameter of the endotracheal tube and the operating pressure of the respirator. The larger the diameter of the endotracheal tube, the lower the required pressure in order to get the same volume of air forced into the lungs. The larger volume accommodated by a large diameter endotracheal tube results in a large volume of un-circulated or dead space gas located between the end of the endotracheal tube inserted into the body of the patient and the respirator. This dead space gas has a high carbon dioxide content, and is forced back into the lungs of the patient during the next inspiration cycle.

In order to reduce the volume of uncirculated or dead space gas contained within the endotracheal tube, a smaller diameter endotracheal tube may be employed. This results in a higher operating pressure of the endotracheal tube in order to force the same volume of air into the lungs of the patient during the same period of time allowed for the inspiration cycle. The higher operating pressure of this type of endotracheal tube requires the use of a diffuser, or other comparable apparatus near the endotracheal tube placed within the patient in order to prevent any damage to the airway, lungs, and the like, as a result of application of high pressure air or oxygen through the endotracheal tube. Whitwam, et al., discloses one approach in which high pressure air pulses are "chopped" and applied to the distal end of an endotracheal tube.

All of the aforementioned endotracheal tubes and monitoring devices employ at least one tube which is used to supply air to the lungs of a patient and withdraw air from the lungs of the patient. Intratracheal pulmonary ventilation(ITPV) developed by Kolobow at the National Institute of Health in Bethesda provides administration of humidified air or oxygen at a continuous flow rate through a catheter which is fed through the endotracheal tube using the apparatus of Cabal, or other suitable devive. This technique is described in:

1. Muller E, Kolobow T, Mandava S & al, Intratracheal Pulmonary Ventilation (ITPV). A new technique to ventilate lungs as small as 12% of normal. Pediatr Res 1991;29(4):326A.

2. Kolobow T, Muller E, Mandava S & al, Intratracheal Pulmonary Ventilation (ITPV). A new technique. Pediatr Res 1991; 29(4):31A.

3. Aprigliano M, Kolobow T, Rossi N & al, Intratracheal Pulmonary ventilation (ITPV) in the management of acute respiratory failure (ARF). Am Rev Resp Dis 1992;145(4):A455.

This ITPV catheter is inserted inside and along the endotracheal tube and its distal tip is positioned near the distal end of the endotracheal tube. The catheter is equipped with a gas flow diffuser at its distal end which is covered by a sleeve. This sleeve reverses the direction of gas flow after it exits the distal tip of the catheter, so that its final direction is away from the lungs. The result is continuous flushing and clearance of most of the un-circulated or dead space volume from carbon dioxide, and reduction in the amount of the gas that is recycled into the lungs during the next inhalation cycle.

SUMMARY OF THE INVENTION

It is therefore an object of the present invention to reduce or flush the dead space gas within the main cavity of an endotracheal tube without significantly affecting the volume of air which may be passed through the endotracheal tube at a given pressure.

It is a further object of the present invention to provide an additional, continuous, or cycled flow of air or oxygen to complement the main flow of air or oxygen mixture through the main cavity of the endotracheal tube.

It is a further object of the present invention to direct this supplementary or complementary air flow so as to maximize the effect of the supplementary or complementary air flow to flush and clear carbon dioxide from the dead space within the endotracheal tube.

In one embodiment, the present invention provides a supplementary air or oxygen flow through an auxiliary tube or lumen, preferably located in the side wall of the endotracheal tube. At the point of entry into the main endotracheal tube, the supplementary air flow is directed away from the lungs of the patient and towards the respirator attached to the endotracheal tube through the use of a curved section located near the end of the endotracheal tube located within the patient. A cuff balloon is preferably employed in order to insure a good seal between the trachea of the patient and the endotracheal tube. In other embodiments, pressure monitoring cavities, audio monitors, and electrocardiogram monitoring devices can be affixed to the endotracheal tube in an appropriate location near the end of the endotracheal tube which is placed within the body of the patient.

DETAILED DESCRIPTION OF A PREFERRED EMBODIMENT

Figure 1:
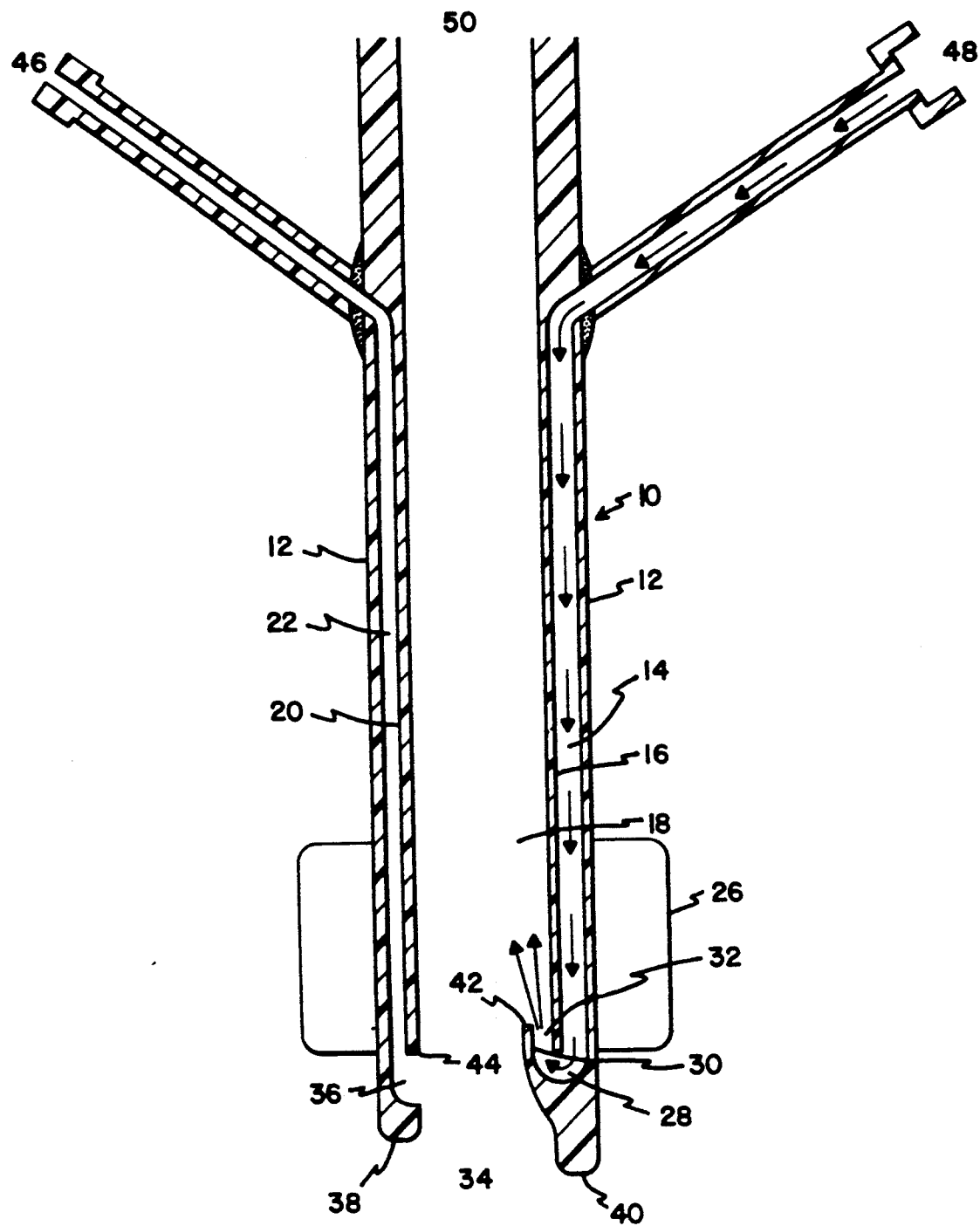
FIG. 1 is a side cross sectional view of the endotracheal tube of the present invention showing intratracheal pulmonary ventilation during exhalation.
Figure 2:
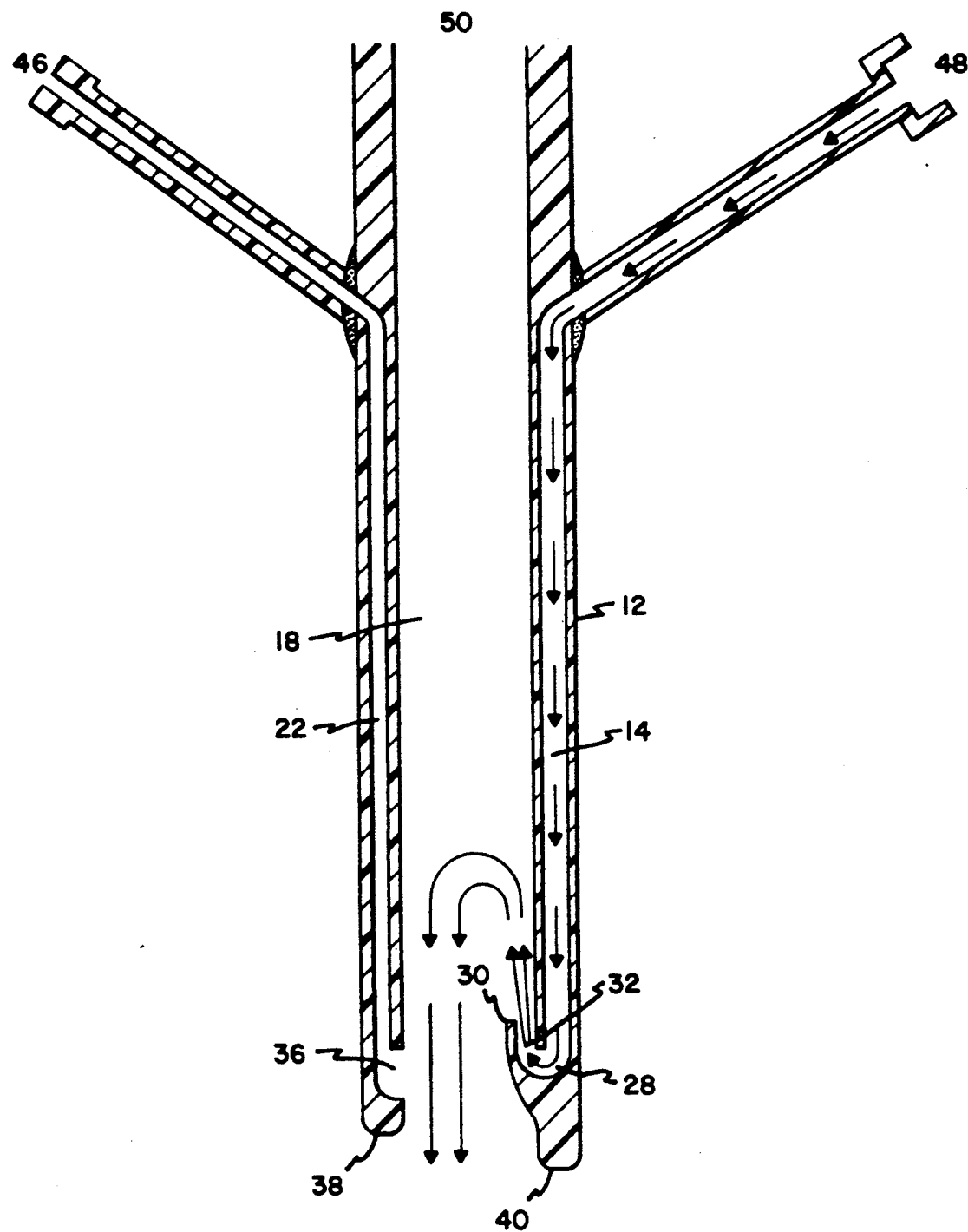
FIG. 2 is a side cross sectional view of the endotracheal tube showing intratracheal pulmonary ventilation during inhalation.
Figure 3:
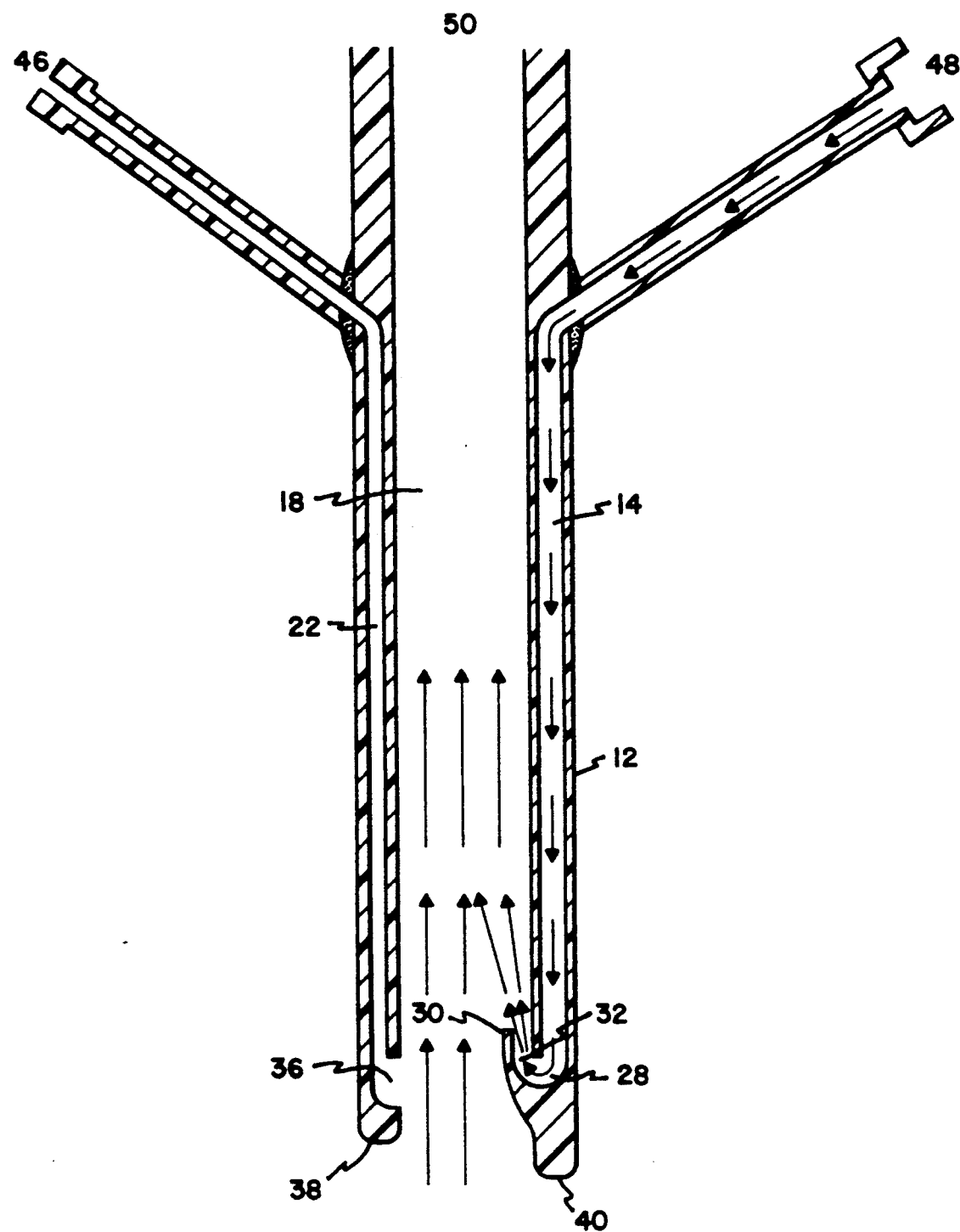
FIG. 3 is a side cross sectional view of the endotracheal tube showing intratracheal pulmonary ventilation during exhalation.

Referring to FIG. 1, one embodiment of the present invention is illustrated having four separate tubes contained within the endotracheal tube 10. The main tube 18 is connected to a ventilator 50 (not shown) which provides an over pressure condition to simulate inspiration, as shown in FIG. 2, and an under-pressure condition to simulate expiration, as shown in FIG. 3.

Main tube 18 is augmented by a second tube 14 which provides intratracheal pulmonary ventilation. This second tube 14 may be connected to a second respirator, or to a continuous flow of air or oxygen 48. If tube 14 is connected to a second respirator, the operation of the second respirator must be complementary to operation of ventilator 50.

In order for the dead space gas between the distal end 34 of the main tube 18 of endotracheal tube 10 and the ventilator 50 to be effectively flushed or removed, and prevented from recycling during the inhalation cycle, it is necessary for the intratracheal pulmonary ventilation tube 14 to produce a flow during the expiration cycle. This is more clearly illustrated in FIG. 3.

The flow of new air or oxygen provided by the intratracheal pulmonary ventilation tube 14 replaces air which would have otherwise been returned to the lungs during the next inspiration cycle of ventilator 50. A continuous flow of intratracheal pulmonary ventilation is shown in FIG. 2, supplementing the inspiration gas mixture provided by ventilator 50, this flow is necessary to displace some of the gas located in the dead space between the distal end 34 and the ventilator 50 of the main tube 18 of endotracheal tube 10, and provide fresh gas to the lungs.

One preferred embodiment of the endotracheal tube of the present invention also has a third tube 22 which has an opening 36 near the distal end 34 of the endotracheal tube. Tube 22 is preferably connected to pressure monitoring equipment and/or gas monitoring equipment 46, in a manner similar to that described in the Broadhurst patent, U.S. Pat. No. 4,850,371. In this manner, the content of the inspired and expired gas can be accurately monitored in order to determine the cardiorespiratory condition of the patient. By providing a separate tube which is connected to the main tube 18 of the endotracheal tube 10, only near the distal end 34 of the endotracheal tube 10, a single, continuous monitoring point is employed for improved accuracy and reliability of the measuring technique.

In the embodiment shown in FIG. 1, a wall 20 is located between tube 22 and main tube 18 of endotracheal tube 10. Similarly, a wall 16 is located between intratracheal pulmonary ventilation tube 14 and the main tube 18 of endotracheal tube 10. An outer wall 12 surrounds the outer perimeter of the endotracheal tube 10.

A cuff balloon 26 is located near the distal end 34 of endotracheal tube 10. Cuff balloon 26 can be inflated through a fourth tube located within the endotracheal tube 10 (this fourth tube is not shown). The pressure within cuff balloon 26 can be maintained at a constant level by a pressure and valving arrangement, or may be monitored by a pilot balloon in a manner similar to that described in Osaki, U.S. Pat. No. 4,334,534.

In the embodiment shown in FIGS. 1-4, the distal end 34 of endotracheal tube 10 has side walls 38 and 40 of differing heights and thicknesses. While it is possible to design an endotracheal tube that has a uniform wall thickness and a uniform length, the present design is preferred, because it locates the intake 36 of the air monitoring tube 22 as close to the lung cavity of the patient as possible, while providing reinforcement and a curved section 28 leading to tab 30 for intratracheal pulmonary ventilation tube 14 near the distal end 34 of the endotracheal tube.

It is possible for intratracheal pulmonary ventilation to be provided through a series of pin holes, or other porous openings along the wall 16 which separates the intratracheal pulmonary ventilation tube 14 from the main tube 18 of the endotracheal tube 10. This technique is not preferred because the goal of introducing intratracheal pulmonary ventilation is to flush gas containing carbon dioxide between the distal end 34 and the ventilator 50 of endotracheal tube 10. Providing an inflow of air or oxygen as close to the distal end 34 of endotracheal tube 10 as possible will maximize the replacement of this un-circulated or dead space gas which would otherwise be forced back into the lungs during inspiration.

Intratracheal pulmonary ventilation tube 14 terminates near the distal end 34 of endotracheal tube 10. A curved section 28 serves to invert the direction of air flow from intratracheal pulmonary ventilation tube 14, directing the flow of air away from the distal end 34 of endotracheal tube 10, towards the ventilator 50. The opening 32 of the intratracheal pulmonary ventilation tube 14 is protected by a sleeve 42 which helps to insure that the flow through intratracheal pulmonary ventilation tube 14 is directed away from the distal end 34 of endotracheal tube 10. The flow of air is illustrated in FIG. 1.

A similar endotracheal tube without the cuff balloon 26 is shown in FIGS. 2-9. The performance and operation of the embodiment of FIGS. 2-9 is similar, if not identical to the operation of the embodiment shown in FIG. 1. The significant difference is that the cuff balloon shown in the embodiment of FIG. 1 provides an air tight seal against the trachea of the patient in order to prevent leakage or seepage of air around endotracheal tube 10 during operation of ventilator 50.

Figure 4:
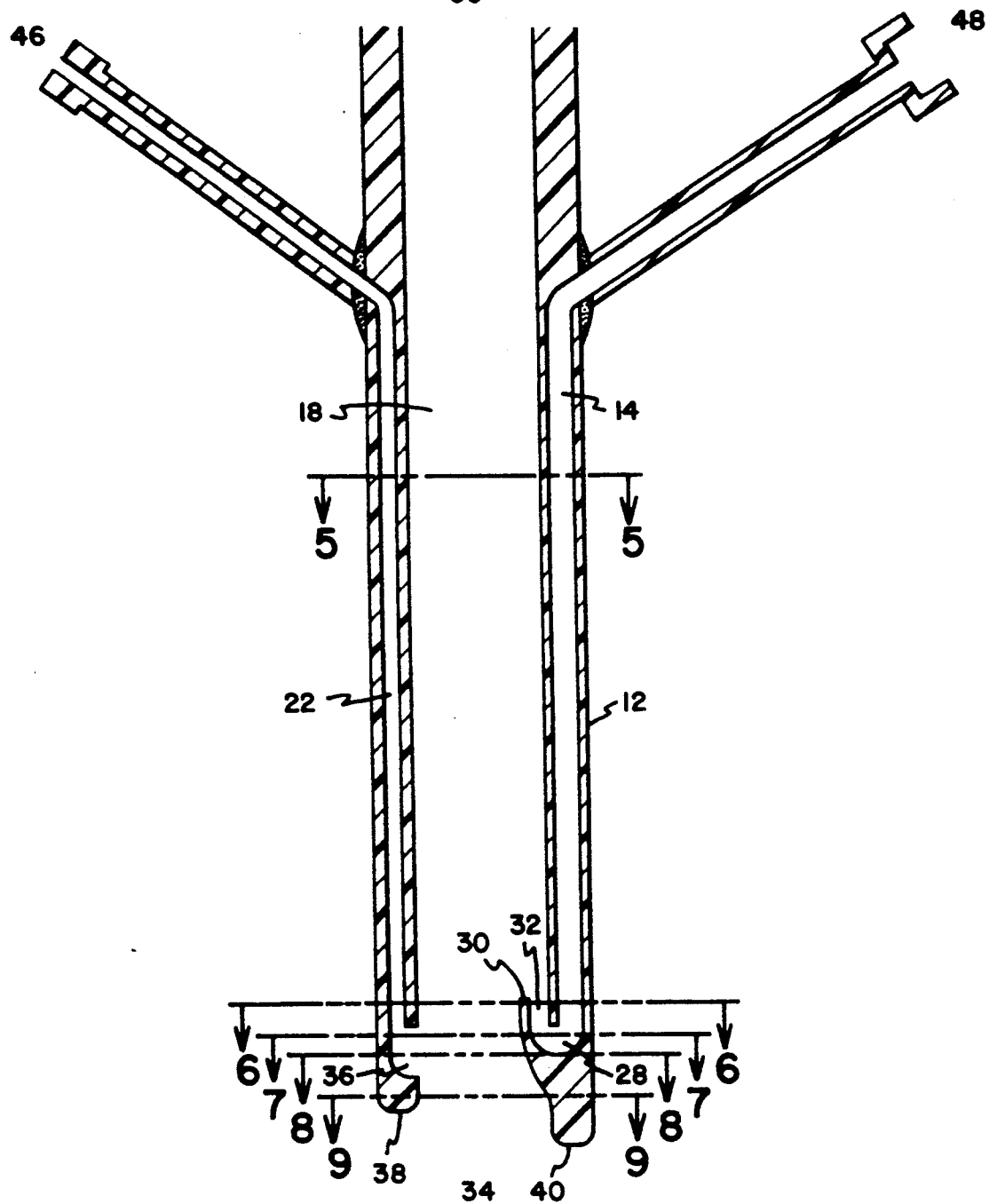
FIG. 4 is a side cross sectional view of the endotracheal tube illustrating the location of lateral cross sectional views shown in FIGS. 5-9.
Figure 5:
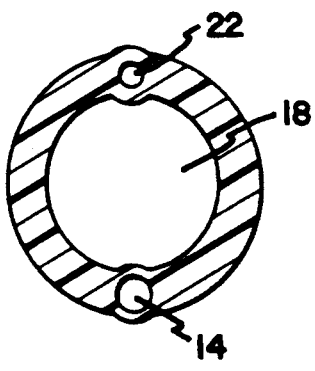
FIG. 5 is a lateral cross sectional view of the endotracheal tube taken at level 1
Figure 6:
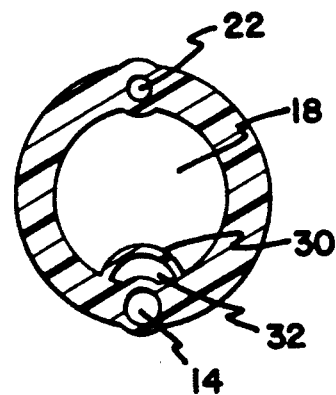
FIG. 6 is lateral cross sectional view of the endotracheal tube taken at level 2.
Figure 7:
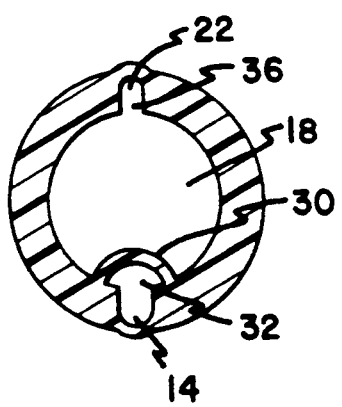
FIG. 7 is a lateral cross sectional view of the endotracheal tube taken at level 3.
Figure 8:
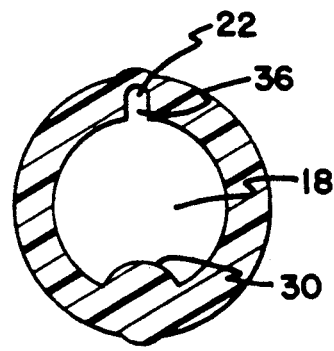
FIG. 8 is a lateral cross sectional view of the endotracheal tube taken at level 4.
Figure 9:
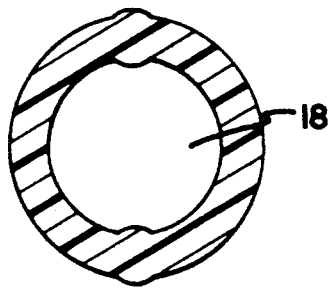
FIG. 9 is a lateral cross sectional view of the endotracheal tube taken at level 5.

To further illustrate the location of the main tube 18, the intratracheal pulmonary ventilation tube 14, and the pressure monitoring tube 22, five lateral cross sectional views taken at levels 1, 2, 3, 4, and 5 of the side cross sectional view of FIG. 4 are shown in FIGS. 5-9, respectively. The lateral cross sectional views of FIGS. 5-9 can be readily augmented with a fourth tube which is connected to cuff balloon 26 in order to provide for inflation of the cuff balloon 26.

By incorporating the intratracheal pulmonary ventilation flow into the endotracheal tube 10, the cross sectional area of main tube 18 is not diminished, and can be used. Kolobow, U.S. Pat. No. 3,734,094, and/or Cabal, U.S. Pat. No. 4,291,691, provide suction to remove mucous or other fluids without interrupting operation of the resuscitator 50 but decrease the internal cross sectional area of the endotracheal tube 10.

Embodiments of the above-described endotracheal tube are designed for use in conjunction with intratracheal pulmonary ventilation. This will serve both for the delivery of gas to the lungs during inspiration, and to clear undesired gas out of the endotracheal tube during expiration. The delivery of intratracheal pulmonary ventilation gas flow of the distal end of the endotracheal tube, and the trachea, is done through a secondary tube which is incorporated into the wall of the main endotracheal tube.

This avoids problems created by introducing an intratracheal catheter into the main endotracheal tube in order to generate intratracheal pulmonary ventilation. The curved section 28 and sleeve 42 serve to invert the direction of gas flow through the intratracheal pulmonary ventilation tube to direct the intratracheal pulmonary ventilation gas flow away from the lungs without requiring an additional catheter to be inserted inside the main tube of the endotracheal tube. Inserting an additional catheter normally increases the airway resistance and decreases the cross section of the main tube available for ventilation, as well as disrupting air flow within the main tube.

Suction of bodily secretions which normally accumulate in the airway during artificial ventilation can be performed without the interruption of intratracheal pulmonary ventilation flow using the endotracheal tube of the present invention.

In one embodiment, the endotracheal tube 10 of the present invention has an outer diameter of 2.175 to 11.5 mm., an internal diameter of 2 to 10 mm. and a wall thickness of 0.175 to 1.5 mm. The overall length must be sufficient to allow the endotracheal tube to be properly located, and is 10 to 50 cm. long depending on the size of the patient.

The intratracheal pulmonary ventilation tube 14 and air monitoring tube 22 are of differing sizes in the embodiment shown. It is recognized that both tubes may be of the same size. In the embodiment shown, the internal diameter of the air monitoring tube 22 is 0.5 to 1.2 mm., and the internal diameter of the intratracheal pulmonary ventilation tube 14 is 0.8 to 2 mm. The length of air monitoring tube 22 and intratracheal pulmonary ventilation tube 14 correspond to the length of endotracheal tube 10. Both the air monitoring tube 22 and intratracheal pulmonary ventilation tube 14 are terminated approximately 6 to 20 mm. above the distal end 34 of endotracheal tube 10.

A cuff balloon 26 is employed with the present invention in those applications where it can be inflated without damaging the airway of the patient. A cuff balloon 26 is typically not employed with infants or small children. The cuff balloon 26 has an inflation tube of a sufficient diameter to permit inflation and deflation of the cuff balloon 26.

The wall thickness of the various tubes is not particularly critical, but must be sufficient to allow leak free operation of each of the tubes. As with ordinary endotracheal tubes, the present invention is formed of a semi-rigid durable plastic suitable for manipulation into the airway of a patient, and has walls which are strong enough to tolerate the operating pressure of a ventilator.

The curved section 28 has the same diameter as the intratracheal pulmonary ventilation tube 14, as can be seen in FIG. 1. It is recognized that a larger diameter curved section 28 may be employed to improve air flow. Sleeve 42 extends beyond curved section 28 by approximately the diameter of the curved section 28, as shown in FIG. 1.

There has been described hereinabove a novel endotracheal tube. Those skilled in the art may now make numerous uses of the present invention by combining it with other techniques known in the art such as pressure monitoring, gas content monitoring, electrocardiogram monitoring, audio monitoring, temperature monitoring, suction techniques for removing accumulated fluids, pressure variable techniques, and the like, without departing from the scope of the present invention which is designed solely by the following claims.

We claim:

1. An endotracheal tube comprising:
   a main tube having an inside, an outside, and proximal and distal ends, said distal end designed to be positioned in the trachea of a patient, said proximal end designed to be attached to a respirator;
   at least one secondary tube having a distal end which terminates substantially adjacent to the distal end of said main tube, said secondary tube substantially parallel to said main tube near said distal end of said main tube;
   at least one opening between said secondary tube and said inside of said main tube located substantially adjacent to the distal end of said secondary tube;
   a tab located on the inside of said main tube between the distal end of said endotracheal tube and the opening between said secondary tube and said main tube, and oriented such that flow through said secondary tube toward the distal end of said secondary tube is directed away from said distal end of said main tube.

2. The device as described in claim 1 in which said tab is conical in shape, having a concave surface facing said distal end of said secondary tube.

3. The device as described in claim 1 and further comprising:
   a cuff balloon, located substantially immediately above the distal end of said main tube and surrounding the outside of the endotracheal tube; and
   at least one tube extending from said cuff balloon away from said distal end of said main tube and fluidly connected to said cuff balloon in order to allow said cuff balloon to be inflated, thus expanding the outer diameter of the endotracheal tube to create a seal between the endotracheal tube and the body of a patient surrounding the endotracheal tube.

4. The device as described in claim 1 and further comprising at least one gas monitoring tube having a distal end located substantially adjacent to the distal end of said main tube, and having at least one opening between the distal end of said gas monitoring tube and said inside of said main tube, near the distal end of said main tube.

5. The device as described in claim 4 and further comprising at least one cuff balloon, located substantially immediately adjacent to the distal end of said main tube, and a tube fluidically connected to said cuff balloon and extending away from said distal end of said endotracheal tube, and located within said endotracheal tube for inflating said cuff balloon in order to create a seal between said endotracheal tube and the body cavity of a patient in which said endotracheal tube is placed.

6. The device as described in claim 1 and further comprising a catheter extending through said main tube from the distal end of said main tube towards the proximal end of said main tube, said catheter having an end positioned substantially adjacent to and extending beyond said distal end of said main tube into the body cavity of a patient for suctioning fluid out of the body cavity of the patient.

7. The device as described in claim 1 in which said proximal end of said main tube is connected to a ventilator and said proximal end of said intratracheal pulmonary ventilation tube is connected to a continuous flow gas supply.

8. An endotracheal tube comprising:
   a main tube having a proximal and a distal end, said distal end designed for insertion into a patient, and preferably positioned in the trachea of the patient, said proximal end designed for attachment to equipment for artificially ventilating the patient in whom the distal end of said main tube is positioned;
   at least one intratracheal pulmonary ventilation tube having a distal end and a proximal end and located within the endotracheal tube, substantially adjacent to, and parallel to said main tube, said distal end of said intratracheal pulmonary ventilation tube located substantially adjacent to said distal end of said main tube, said proximal end of said intratracheal pulmonary ventilation tube extending toward said proximal end of said main tube;
   at least one opening between said intratracheal pulmonary ventilation tube and said main tube near the distal end of said intratracheal pulmonary ventilation tube and said distal end of said main tube; a tab located on the inside of said main tube between the distal end of said endotracheal tube and the opening between said intratracheal pulmonary ventilation tube and said main tube, and oriented such that flow through said intratracheal pulmonary ventilation tube toward the distal end of said intratracheal pulmonary ventilation tube is directed away from said distal end of said main tube;
   said opening between said distal end of said intratracheal pulmonary ventilation tube and said distal end of said main tube further comprising a curved section of said intratracheal pulmonary ventilation tube.

9. The device as described in claim 8 and further comprising a cuff balloon located substantially immediately adjacent to said distal end of said main tube, between said distal end of said main tube and said proximal end of said main tube, said cuff balloon surrounding the outer surface of the endotracheal tube; and
   at least one cuff balloon inflation tube fluidically connected to said cuff balloon and extending toward said proximal end of said main tube for inflating said cuff balloon to reduce the flow of air and other gases and fluids on the outside of said endotracheal tube once said endotracheal tube is inserted in the desired cavity within the patient and said cuff balloon is inflated.

10. The device as described in claim 9, and further comprising at least one pressure monitoring tube having a proximal and distal end, said distal end of said pressure monitoring tube located substantially immediately adjacent to said distal end of said main tube, said proximal end of said pressure monitoring tube located near the proximal end of said main tube;

at least one opening between the distal end of said pressure monitoring tube and the distal end of said main tube, allowing pressure near said distal end of said main tube to be monitored near the proximal end of said pressure monitoring tube.

11. The device as described in claim 9, and further comprising at least one gas content monitoring tube having a proximal and distal end, said distal end of said gas monitoring tube located substantially immediately adjacent to said distal end of said main tube, said proximal end of said gas monitoring tube located near the proximal end of said main tube;

at least one opening between the distal end of said gas monitoring tube and the distal end of said main tube, allowing samples of the gas located near the distal end of said main tube to be drawn into said gas monitoring tube.

12. The device as described in claim 11 in which the diameter of said main tube is at least twice the diameter of said intratracheal pulmonary ventilation tube;

the diameter of said cuff balloon inflation tube being less than one-third of the diameter of said main tube; and the diameter of said gas monitoring tube being less than one-third of the diameter of said main tube.

13. The device as described in claim 8 and further comprising a catheter extending through said main tube from the distal end of said main tube towards the proximal end of said main tube, said catheter having an end positioned substantially adjacent to and extending beyond said distal end of said main tube into the body cavity of a patient for suctioning fluid out of the body cavity of the patient.

14. The device as described in claim 8 in which said proximal end of said main tube is connected to a ventilator and said proximal end of said intratracheal pulmonary ventilation tube is connected to a continuous flow gas supply.

* * * * *

UNITED STATES PATENT AND TRADEMARK OFFICE
CERTIFICATE OF CORRECTION

PATENT NO. : 5,291,882
DATED : March 8, 1994
INVENTOR(S) : Imad R. Makhoul et al It is certified that error appears in the above-indentified patent and that said Letters Patent is hereby corrected as shown below:

Column 3, line 12, after "suitable" and before the period ("."), "devive" should read --device--.

Signed and Sealed this

Eighth Day of November, 1994

Attest:

BRUCE LEHMAN

Attesting Officer      Commissioner of Patents and Trademarks